United States Patent [19]

Mori

[11] Patent Number: 4,766,899
[45] Date of Patent: Aug. 30, 1988

[54] SOLAR RAY ENERGY RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 1,296

[22] Filed: Jan. 8, 1987

[30] Foreign Application Priority Data

Jan. 16, 1986 [JP] Japan .................................. 61-6973

[51] Int. Cl.$^4$ .............................................. A61N 3/00
[52] U.S. Cl. ..................... 128/397; 362/32; 128/372
[58] Field of Search ............... 128/395, 396, 372, 397, 128/398, 82.1, 375; 250/504, 504 H; 33/227; 604/20; 362/32

[56] References Cited

U.S. PATENT DOCUMENTS

| | | | |
|---|---|---|---|
| 2,085,627 | 6/1937 | Bodnar | 250/504 |
| 2,560,652 | 7/1951 | Landaver | 128/396 |
| 3,818,914 | 6/1974 | Border | 128/396 |
| 4,505,545 | 3/1985 | Salia-Munoz | 128/395 |
| 4,605,280 | 8/1986 | Welber et al. | 128/396 |

Primary Examiner—Richard C. Pinkham
Assistant Examiner—Mark S. Graham
Attorney, Agent, or Firm—Jordan and Hamburg

[57] ABSTRACT

A solar ray energy radiation device for use in medical treatment comprises a transparent or semi-transparent cylindrical member, a cover member for closing off one end surface of the cylindrical member, and an optical conductor cable having a light ray emitting end placed on the cover member. The solar ray energy transmitted through the optical conductor cable is radiated from the light ray emitting end into the cylindrical member. An open-ended side of the cylindrical member is facing the treatment area in order to administer solar ray energy onto a person receiving treatment. The cylindrical member is comprised of at least two cylindrical portions which are capable of sliding telescopically within one another in the direction of the axis of the cylindrical member.

2 Claims, 2 Drawing Sheets

SOLAR RAY ENERGY RADIATION DEVICE FOR USE IN MEDICAL TREATMENT

BACKGROUND OF THE INVENTION

The present invention relates to a solar ray energy radiation device for use in medical treatment, in particular, a light ray radiation device which radiates light ray energy that corresponds to the visible light ray components of solar rays. These light rays are directed to a diseased part of or a desired portion of a patient's body as a form of medical treatment; or are radiated onto the surface of a person's skin as a form of beauty treatment or for the promotion of a person's general health.

In recent years, a large number of persons suffer from incurable diseases such as arthritis, neuralgia and rheumatism, or from pain caused by an injury scar, a bone fracture scar or mysterious pain from an unkown cause. Furthermore, persons cannot avoid having their skin show signs of aging which progresses gradually from a comparatively young age. On the other hand, the present applicant has previously proposed focusing solar rays or artificial light rays by the use of lenses or the like, and to guide the same into an optical conductor, then to transmit them onto an optional desired place through the optical conductor. Those light rays transmitted in such a way are employed for use in illumination or for other like purposes, as for example, to cultivate plants, chlorella, or the like. In such a process, visible light rays not containing harmful ultraviolet or infrared rays, promote health and also prevent a person's skin from aging. Furthermore, the effects of those visible light rays are very noticeable in giving patients relief from arthritis, neuralgia, bedsores, rheumatism, injurty scars, bone fracture scars, or the like, as well as for alleviating pain from those same diseases. Such results have been corroborated by the present applicant's own experience.

On the basis of the afore-mentioned discovery, the present applicant has previously proposed in various ways a light ray radiation device for use in medical treatment capable of radiating the light rays that correspond to the visible light ray components of solar rays but not containing therein harmful components such as ultraviolet rays and infrared rays.

In the solar ray energy radiation device for use in medical treatement as mentioned above, the radiation intensity needs to be changed in accordance with each individual patient's condition. However, the end portion of the optical conductor needs to be put at a predetermined distance from the diseased part of the patient in order to maintain the radiation's intensity at a predetermined level, and therefore the patient has to let one's diseased part become stationary from keeping the above-mentioned distance therebetween. But it is very difficult to maintain such a position during treatment of the diseased part.

SUMMARY OF THE INVENTION

It is an object of the present invention to provide a solar ray energy radiation device for use in medical treatment capable of easily keeping the radiation device at a predetermined distance from a diseased part.

It is another object of the present invention to provide a solar ray energy radiation device for use in medical treatement capable of easily adjusting the intensity of the radiation applied to a diseased part of a patient.

The above-mentioned features and other advantages of the present invention will be apparent from the following detailed description which goes with the accompanying drawings.

DESCRIPTION OF THE PREFERRED EMBODIMENTS

Figure 1:
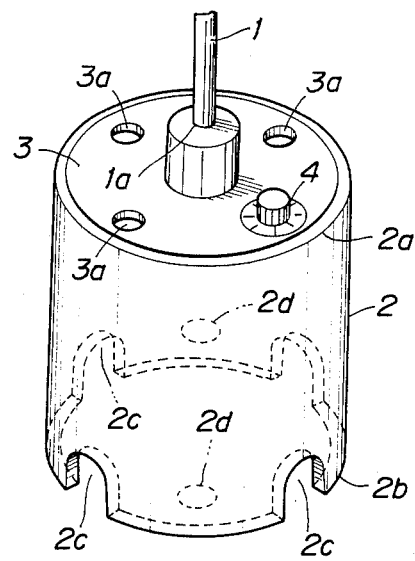
FIGS. 1 and 2 are, respectively, construction views for explaining embodiments of a solar ray energy radiation device for use in medical treatment previously proposed by the present applicant.

FIG. 1 is a construction view for explaining an embodiment of a light ray radiation device for use in medical treatment according to the present invention. In FIG. 1, 1 is an optical conductor cable. Solar rays or artificial light rays are guided into the optical conductor cable 1 from the end portion thereof transmitted therethrough. The light rays (the white-colored light rays) corresponding to the visible light ray components of solar rays are transmitted through an optical conductor cable 1 in such a manner as was previously proposed in various ways by the present applicant. 2 is a semi-transparent or transparent cylindrical member attached to the optical conductor cable 1 at the light ray emitting side 1a thereof, and 3 is a cover member for closing off one end 2a of the cylindrical member 2. The light ray emitting end 1a of the optical conductor cable 1 is placed at approximately the central portion of the cover member 3. Solar ray energy transmitted throught he optical conductor cable 1 is channeled into the cylindrical member 2.

At the time of its use for medical treatment, another end 2b of the cylindrical member 2 is brought in line with the position for medical treatment or placed opposite the same at a desired distance. The light rays, consisting of visible light rays, transmitted through the optical conductor cable 1, as mentioned before, are focused onto a diseased part, a desired portion of a patient's body, or other various parts of the human body. As mentioned above, the light rays to be radiated onto a diseased part of a patient are light rays corresponding to the visible light ray components of solar rays which contain neither ultraviolet nor infrared rays. Thereby, it is possible to administer medical treatment without the patient suffering from any harmful effects of ultraviolet or infrared rays.

With respect to the above-mentioned light rays radiation device for use in medical treatment, since the cylindrical body 2 is constructed of a semi-transparent or transparent substance, the position of the light rays being radiated and the approximate intensity of the light rays can be assured by observing both of them with the naked eye. However, in the case of bringing the end portion 2b of the cylindrical member 2 into close contact with the diseased area or a desired portion of a patient, there is a fear that the inner wall of the cylindrical member 2 will become fogged up as a result of moisture in the form of vapor or sweat being discharged from the patient's skin, or the like, and thereby causing the interior of the cylindrical member 2 not to be visible from the outside. Furthermore, the patient's skin will not be able to breathe because the interior of the cylindrical member 2 will be filled with moisture.

In order to solve such a problem, in the case of the embodiment shown in FIG. 1, notches 2c are formed at the end portion side 2b of the cylindrical member 2 or through-holes 2d are formed on the side wall of the cylindrical member 2 so as to pass therethrough, and further, through-holes 3a are formed on the cover member 3. In such a construction, air can flow freely into the cylindrical member 2, and therfore it will be possible to prevent the interior of the cylindrical member 2 from becoming fogged up or from being filled with moisture.

Furthermore, in the case of administering medical treatment by radiating solar ray energy onto the diseased part or the desired portion of a patient as mentioned above, the time period of radiation will differ according to the condition of the patient. It is troublesome to keep watch on the radiation time period. A time 4 is employed for setting up the above-mentioned radiation time period. The time period to be set up is recorded on a card or the like not shown in FIG. 1. For example, it is recorded thereon for every phase of the diseased condition. By refering to the card, the patient can set up the radiation time period needed. When the time 4 measures (counts) the set-up time period, it sends out an alarm sound or turns on a lamp for informing the patient that the set-up time period has elapsed.

Figure 2:
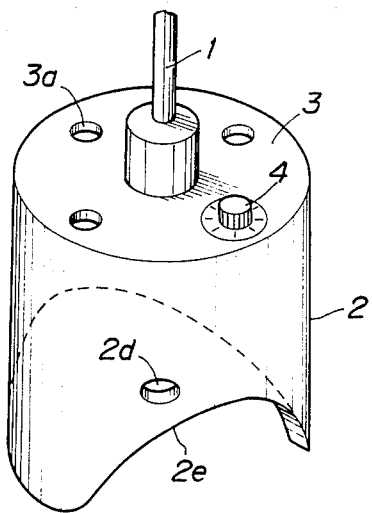

FIG. 2 is a construction view for explaining the other embodiment of a solar ray energy radiation device which has been previously proposed by the present applicant. In this embodiment, the end portion 2b of the cylindrical member 2 is formed in a shape 2e corresponding to that of a limited portion, upon which solar ray energy is administered. In the case of the embodiment shown in FIG. 2, the shape 2e is so formed that the diameter thereof coincides with that of the arm or the leg of a person. Thereby, it is possible to apply solar ray energy effectively onto the uneven skin surface of a person, namely, to radiate the same onto the diseased part of such skin surface without allowing the solar ray energy to leak outside of the device. Moreover, in FIG. 2, the part performing the same action as that in the embodiment shown in FIG. 1 is represented by the same reference numeral.

In the solar ray energy radiation device for use in medical treatment as mentioned above, the radiation intensity needs to be changed in accordance with each individual patient's condition. However, in the aforementioned device, the end portion 2b of the cylindrical body 2 needs to be put at a predetermined distance from the diseased part of the patient in order to change the radiation's intensity, and therfore the patient has to let one's diseased part become stationary for keeping the above-mentioned distance therebetween. Such a position can be very troublesome.

Figure 3:
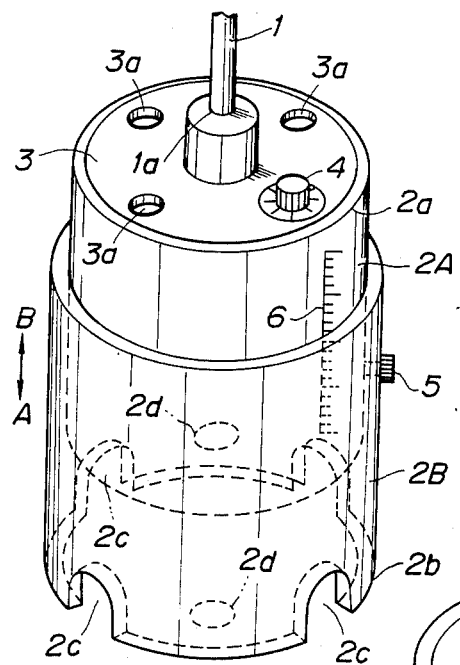
FIGS. 3 and 4 are, respectively, construction views for explaining embodiments of a solar ray energy radiation device for use in medical treatment according to the present invention.
Figure 4:
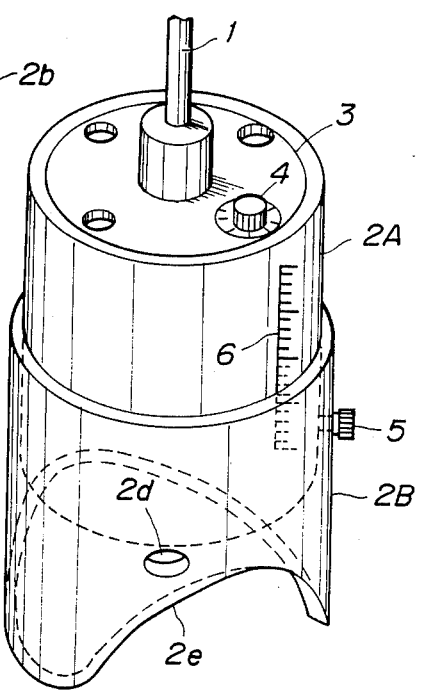

FIGS. 3 and 4 are, respectively, construction views for explaining embodiments of a solar ray energy radiation device for use in medical treatment according to the present invention. In FIGS. 3 and 4, the portion performing the same action as that in the embodiment shown in FIGS. 1 and 2 is represented by the same reference numeral.

In the present invention, a cylindrical member 2 is divided into at least two portions 2A and 2B as shown in FIGS. 3 and 4. Those portions are capable of sliding in a direction along the axis thereof and are fixed in a desired position by use of a fixing screw 5. In both figures, 6 is a scale for memorizing the relative position of the cylindrical bodies 2A and 2B at the time of fixing them. In consequence, the device can be employed as follows. When the radiation intensity needs to be increased, the cylindrical member 2B is slid in a direction shown by an arrow A so as to shorten the distance between the light ray emitting end of the optical conductor cable 1 and the diseased part of the patient. On the contrary, when the radiation intensity needs to be decreased, 2B is slid in an opposite direction shown by an arrow B so as to extend the distance therebetween. In such a manner as mentioned above, even though the intensity of the light rays is changed, the end portion of the cylindrical member 2B always comes into contact with the diseased part of the patient. Furthermore, the device can be employed by keeping the position and the angle fixed. Therefore, it is possible to move the radiation device together with the diseased part as long as the end portion 2b of the cylindrical member 2B is kept in contact with the diseased part. Consequently, this new radiation device doesn't give the patient a feeling of being cramped.

Although the embodiment employing the cylindrical member 2, divided into two portions has been described heretofore, the present invention is not limited to the abovementioned embodiment. It can be easily understood that the cylindrical member 2 can be divided into more than two optional desired portions.

As is apparent from the foregoing description, according to the present invention, the adjustment of the intensity of the light rays can be done easily, and furthermore it is possible to provide a solar ray energy radiation device for use in medical treatment which can be employed conveniently with little loss of light ray energy.

I claim:

1. A solar ray energy radiation device for use in medical treatment comprising a transparent or semi-transparent cylindrical means, a cover member closing off one longitudinal end of said cylindrical means, an optical conductor cable having a light ray emitting end placed through said cover member, in which solar ray energy, transmitted through said optical conductor cable, is radiated from said light ray emitting end into said cylindrical means, the other longitudinal end of said cylindrical means being open and facing the treatment area in order to administer solar ray energy onto a person receiving treatment, said cylindrical means comprising at least two cylindrical portions which are capable of sliding telescopically within one another in the direction of the axis of said cylindrical means, and a fixing screw mounted on said cylindrical means operable to fix said two cylindrical portions in a desired position.

2. A solar ray energy radiation device for use in medical treatment as defined in claim 1, wherein said cylindrical portion which is positioned on the inside has a scale on the surface thereof for indicating the relative position of said two cylindrical portions at the time of fixing them in a desired position.

* * * * *